United States Patent [19]

Pletcher

[11] Patent Number: 4,559,012
[45] Date of Patent: Dec. 17, 1985

[54] ORTHODONTIC BRACKET

[76] Inventor: Erwin C. Pletcher, P.O. Box 3054, Rancho Santa Fe, Calif. 92067

[21] Appl. No.: 678,707

[22] Filed: Dec. 6, 1984

[51] Int. Cl.[4] .............................................. A61C 7/00
[52] U.S. Cl. .................................................... 433/10
[58] Field of Search .............................. 433/10, 13, 11

[56] References Cited

U.S. PATENT DOCUMENTS 4,077,126  3/1978  Pletcher ................................. 433/10
4,371,337  2/1983  Pletcher ................................. 433/10
4,419,078  12/1983 Pletcher ................................. 433/10

Primary Examiner—Robert Peshock
Attorney, Agent, or Firm—Christie, Parker & Hale

[57] ABSTRACT

An orthodontic bracket assembly with a locking member rotatably mounted on a slotted bearing member configured to receive an arch wire. The locking member is rotatable to capture the arch wire in the bracket assembly. A detent is provided to secure the locking member in a closed position.

9 Claims, 11 Drawing Figures

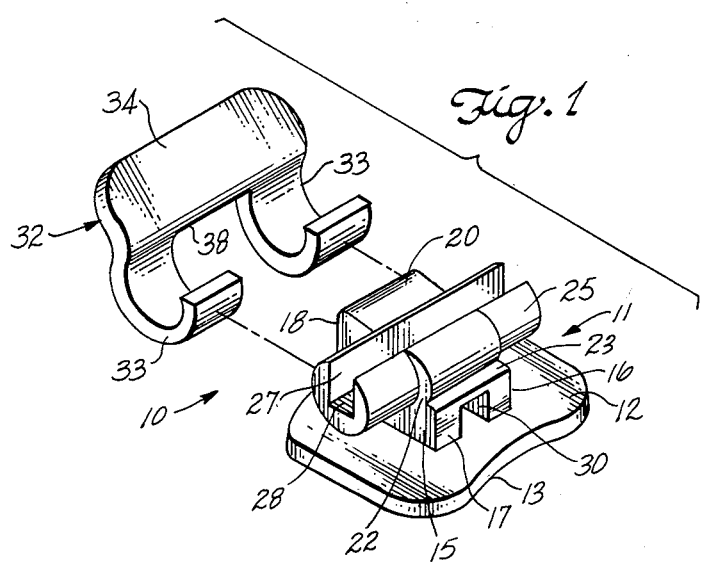
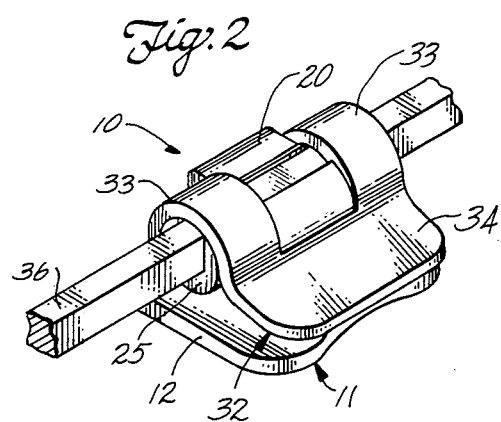
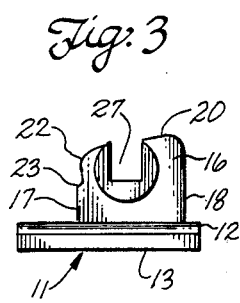
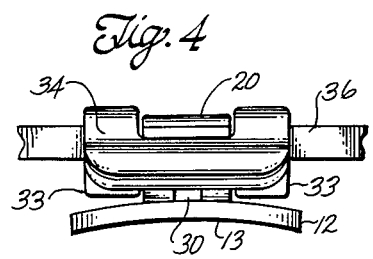
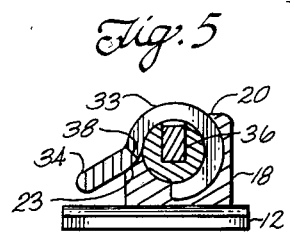
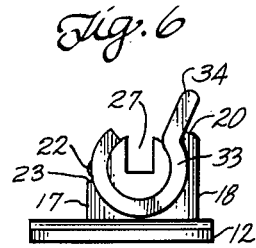

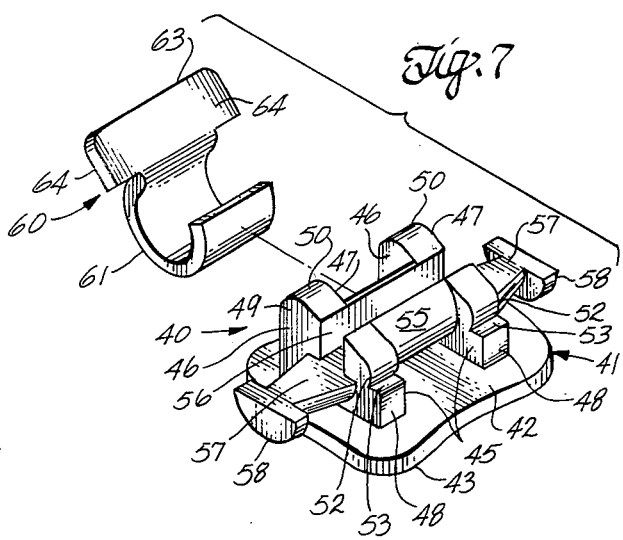
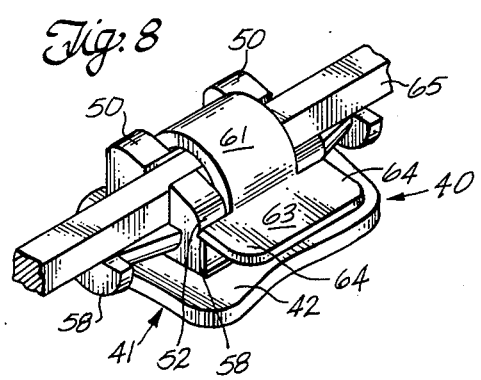
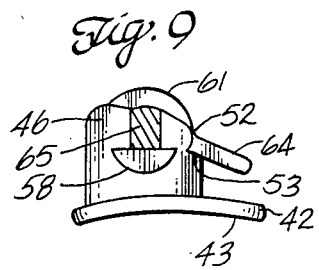
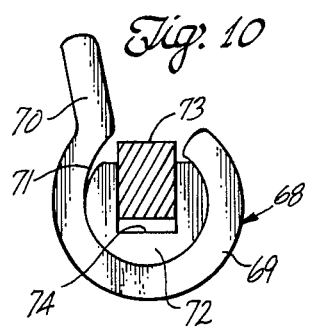
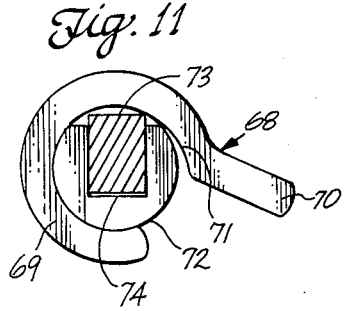

ORTHODONTIC BRACKET

BACKGROUND OF THE INVENTION

Several versions of self-locking orthodontic brackets are shown in my U.S. Pat. Nos. 4,077,126, 4,371,337, and 4,419,078, the disclosures of which are incorporated herein by reference. The reader is referred to these patents for a general description of the function of an orthodontic bracket, and the advantages gained by using a rotatable locking member which eliminates (or at least minimizes) the need for tie or ligature wires to secure an arch wire to the bracket. The present invention is directed to a similar bracket which incorporates various refinements, including an improved detent lock for the bracket locking member when in the closed position.

SUMMARY OF THE INVENTION

This invention relates to a self-locking orthodontic bracket assembly which largely eliminates the need for time-consuming installation of tie or ligature wires used to secure an arch wire to a conventional bracket. The assembly includes a bracket body having a base for attachment to a tooth or tooth band. Extending from the base is a structure which includes a cylindrical bearing member, and a forwardly open arch-wire slot extends through the bearing member. A locking member is rotatably fitted on the bearing member, and is movable between open and closed positions to receive and then lock an arch wire in the slot.

A particular feature of the invention is the incorporation of cooperating portions of the bracket body and locking-member handle to provide a detent lock and positive stop for the handle in the closed position. These cooperating portions are configured so the bracket body is particularly well suited for casting in metal or injection molding in plastic. The locking member is made of an elastically deformable resilient metal or plastic material which enables passage of the handle over the detent protrusion, and fitting of the locking member over the bearing member.

DESCRIPTION OF THE DRAWINGS

FIG. 1 is an exploded pictorial view of a first embodiment of an orthodontic bracket according to the invention;

FIG. 2 is a pictorial view of the assembled bracket components shown in FIG. 1;

FIG. 3 is a side view of the bracket body;

FIG. 4 is a top view of the bracket assembly;

FIG. 5 is a view similar to FIG. 3, but with a locking member installed on the bracket body, and rotated to an open position;

FIG. 6 is a view similar to FIG. 5, but in section and with the locking member rotated to a closed position;

FIG. 7 is an exploded pictorial view of a second embodiment of an orthodontic bracket according to the invention;

FIG. 8 is a pictorial view of the assembled bracket components shown in FIG. 7;

FIG. 9 is an end view of the bracket assembly shown in FIG. 8;

FIG. 10 is a side view of a modified locking handle for the bracket assembly; and FIG. 11 is a view similar to FIG. 10, but with the locking handle rotated to a closed position.

DESCRIPTION OF THE PREFERRED EMBODIMENTS

FIGS. 1–6 show a first embodiment of an orthodontic bracket assembly 10 according to the invention. The bracket assembly includes a bracket body 11 having a base 12 with a rear or tooth-facing surface 13 adapted for attachment to a tooth. The bracket base may be welded to a conventional tooth band (not shown) for cemented attachment to a tooth, or alternatively the base can be provided with a mesh or other conventional base configuration for direct cemented attachment to the tooth.

The portion of the bracket body extending forwardly from base 12 is a block-like structure having side surfaces 15 and 16, gingival and occlusal surfaces 17 and 18, and a front surface 20 which slopes slightly toward the base as it extends from the occlusal surface toward the gingival surface. The gingival end of front surface 20 extends first gingivally, and then slightly occlusally to form an elongated shoulder-like detent "bump" or protrusion 22. A shelf or ledge at the lower or inner end of the detent protrusion or shoulder defines a stop surface 23 extending from the protrusion to gingival surface 17.

A pair of bearing members 25, having at least portions which are cylindrical in shape, extend mesiodistally from opposite side surfaces 15 and 16 of the bracket body. An arch-wire-receiving slot 27 extends into the bearing members and bracket body, and the slot extends to an end wall 28. Preferably, the central part of the bracket body also includes a vertically extending slot 30 immediately adjacent bracket base 12, and the slot serves as a socket to receive pins or other auxilliary attachments, or to provide a convenient anchorage for a ligature wire should ligation be necessary in a preliminary treatment stage when the arch wire cannot be fully seated in the bracket slot.

A locking member 32 has a hub formed by a pair of coaxial and axially spaced partial rings 33, the periphery of each ring extending around more than 180°. The inside diameter of rings 33 is selected to give the locking member a smooth rotatable fit on the bracket body when the rings are fitted over bearing members 25 as shown in FIG. 2. Rings 33 are joined by an integrally formed and outwardly extending handle 34.

Bracket body 11 may be an injection-molded plastic part, a machined stainless-steel component, or a cast metal component, casting being the presently preferred production method. In the preferred form, all of the components of the bracket body are integral, but it is also practical to form bearing members 25 as a separate slotted rod which is then brazed or welded to a receiving socket in the bracket body. Locking member 32 may be made of either plastic or metal, but should be formed of a slightly resilient material so rings 33 are elastically deformable and can expand slightly to receive the bearing members when the locking member is snapped in place on the bracket body.

FIG. 5 shows the bracket assembly with the locking member in an open position prior to installation of an arch wire 36 (FIGS. 2, 4 and 6). Further clockwise (as seen in FIG. 5) rotation of the locking member in the opening direction is blocked by front surface 20 which abuts handle 34 of the locking member to insure that the locking member cannot be overrotated into a position which would partially block the arch-wire slot.

If desired, front surface 20 of the bracket body can be raised slightly to adjust the position of the limit stop so the locking-member handle extends directly out from a side surface of the open arch-wire slot. In this configuration, the locking-member handle serves as a convenient shelf on which to rest the arch wire prior to installation in the arch-wire slot, and also helps to guide the arch wire directly into the slot. The position of the limit stop can also be adjusted to accommodate different angulations of the arch-wire slot which may be provided to enable the bracket to apply a torque force to the tooth to which the bracket assembly is attached.

After the arch wire is installed, the locking member is simply rotated to a closed position as shown in FIGS. 2, 4 and 6. During the last part of the rotation toward the closed position, an inner part 38 of the locking-member handle between rings 33 is forced to ride elastically over detent protrusion 22 before snapping down against stop surface 23. This interference-fit snap action provides a definite tactile signal to the orthodontist that the bracket has been properly closed, and also insures that the locking member will not become inadvertently opened by the patient during chewing of food or the like. The resiliency of the locking-member handle enables it to ride over the detent protrusion, and the resulting restoring force provides the desired snap action as the locking member is further rotated into the fully seated and closed position against stop surface 23.

FIGS. 7–9 show a second embodiment of the invention which is a bracket assembly 40. This assembly has a bracket body 41 with a base 42 having a rear or tooth-facing surface 43 adapted for attachment to a tooth as already described. The bracket body further defines a pair of mesiodistally spaced block-like structures 45 extending forwardly from base 42.

Each structure 45 is generally similar in shape, but narrower than the corresponding structure in bracket body 11 described above. That is, each of the structures has side surfaces 46 and 47, gingival and occlusal surfaces 48 and 49, and a front surface 50 which slopes slightly toward the base as it extends from the occlusal surface toward the gingival surface. The gingival end of front surface 50 extends first gingivally, and then slightly occlusally to form an elongated detent "bump" or protrusion 52. A shelf or ledge at the lower or inner end of the detent protrusion defined a stop surface 53 extending from the protrusion to gingival surface 48.

A generally cylindrical bearing member 55 extends between the two structures 45, and an arch-wire slot 56 is machined or cast into both the bearing member and the adjacent portions of structures 45. As an optional feature, mesiodistal extensions 57 may be formed on the outer surfaces of structures 45, and each extension preferably has a small rearwardly facing head 58 at its end. Extensions 57 provide a long bearing surface for the arch wire to enable good control over rotational movements of a tooth, and heads 58 provide a convenient anchor point for a ligature wire if ligation is necessary because the arch wire cannot be completely seated in the bracket during an early treatment stage.

Bracket assembly 40 also includes a locking member 60 having a partial ring 61, the circumference of which extends slightly more than 180°. As in the first embodiment described above, the inside diameter of ring 61 is selected to make a smooth rotatable fit over the outside diameter of bearing member 55. A handle 63 is integrally formed with ring 61, and tips 64 of the handle extend mesiodistally beyond the opposite end surfaces of the ring.

As already described, the bracket body can be either cast or machined, but is preferably formed as a metal casting for economical production. Locking member 60 can be cast of a resilient plastic material, or formed from a resilient spring-metal material. Resiliency of the locking member is important to enable ring 61 to be snapped in place over the bracket-body bearing member, and also to provide the desired detent action described below.

The complete bracket assembly is shown in FIG. 8, with an arch wire 65 installed in the bracket, and locking member 60 rotated to a closed position. As in the first embodiment, front surface 50 of the bracket body provides a stop for the locking member when it is rotated to an open position. Similarly, rotation of the locking member to a closed position (FIGS. 8 and 9) forces handle tips 64 over protrusions 52 until the handle "detents" into a fully closed and locked position with tips 64 resting against stop surfaces 53.

Although the locking-member rings described above have generally cylindrical inner surfaces, the entire inner surface need not be cylindrical, and an alternative embodiment of a modified locking member 68 is shown in FIGS. 10 and 11. In common with the locking members already described, members 68 has at least one partial ring 69 with a handle 70 extending therefrom. As shown in the drawings, a portion 71 of ring 69 adjacent handle 70 has a larger radius of curvature than the remaining interior surface of the ring, providing a slight clearance space between a bearing member 72 and the handle end of the ring.

The advantage of this style of locking member is that it makes it easy to rotate the member over an arch wire 73 which is not fully seated in a bearing-member slot 74 during initial installation. As the locking member is rotated toward the closed position, portion 71 forces the arch wire into the slot without requiring any additional manipulation by the orthodontist.

Directional terminology used herein (such as gingival, occlusal, and the like) is intended to apply to the bracket as conventionally mounted on a labial or outer face of a tooth, with the locking member being adjacent the gum tissue when in a closed position. The bracket, however, is very compact and smoothly configured, and is therefore well suited for other orientations, or for attachment on the lingual or inner tooth surface. It is to be understood that appropriate adjustments in terminology are necessary depending on the bracket placements selected by the orthodontist, and the terms used herein are merely illustrative rather than limiting.

There has been described an orthodontic bracket which is self-locking, and when eliminates the need for ligature wires in most or all phases of conventional orthodontic treatment. The bracket is physiologically clean, and is configured to enable economical and rapid manufacture and assembly. The embodiments described are particularly advantageous in that they provide a secure action of the locking member in the closed position, thereby minimizing the risk of inadvertent opening of the arch-wire slot after the arch wire has been installed and fully seated.

What is claimed is:

1. An orthodontic bracket assembly, comprising:
   a bracket body having a base, the body defining a bearing member having a slot to receive an arch wire, the body further having a surface forming a ledge, the surface extending first away from the base, slot and ledge, and then toward the slot to form a detent; and a locking member with a hub having a mesiodistal passage therethrough configured to receive the bearing member so the hub fits captively and rotatably over the bearing member, the hub having a mesiodistal slot extending therethrough into communication with the passage, and further having a handle extending therefrom;

the locking member being movable between an open position to receive the arch wire through the hub slot into the arch wire slot, and a closed position which misaligns the hub and arch-wire slots to capture the arch wire in the bracket assembly, the locking-member handle making an interference fit over the detent to rest against the ledge in the closed position.

2. The assembly defined in claim 1, wherein the locking member is integrally formed of a resilient material enabling the hub to be elastically deformed when fitted over the bearing member, and the handle to be elastically deformed when passing over the detent.

3. The assembly defined in claim 2 wherein the locking-member hub slot is formed so the undeformed hub extends more than 180° around the bearing member.

4. The assembly defined in claim 3 wherein the bracket body has a front surface which slopes toward the base as the surface extends toward the detent, the front surface acting as a limit stop for the locking member in the open position.

5. The assembly defined in claim 3 wherein the locking member hub enlarges in internal diameter adjacent the handle to enable the locking member to be closed over an arch wire which is incompletely seated in the arch-wire slot.

6. The assembly defined in claim 3 wherein the bracket body is a casting which integrally forms the body, base, and bearing member.

7. A self-locking orthodontic bracket, comprising:

a bracket body having a base with a rear toothfacing surface, the body extending forwardly from the base and having a pair of generally mesiodistally extending bearing members extending from opposite side surfaces thereof above the base, the body defining an open-ended arch-wire slot extending between and through the bearing members; and a locking member having a pair of spacedapart hubs with mesiodistal passages therethrough to receive the bearing members so the hubs fit captively and rotatably over the bearing members, the hubs being deformable to enable installation over the bearing members, the hubs each having a slot extending therethrough into communication with the passage, and a handle joining and extending between the hubs;

the locking member being rotatable on the bearing member between open and closed positions, the open position aligning the slots to enable seating of an arch wire in the body slot, and the closed position placing the hub slot out of alignment with the body slot to capture the arch wire within the bracket assembly.

8. The assembly defined in claim 7, wherein the bearing members are generally cylindrical in cross section, and the hub slots are formed so the undeformed hubs extend more than 180° around the respective bearing members.

9. The assembly defined in claim 8, wherein the body has a surface forming a ledge, the surface extending away from the base, slot and ledge, and the toward the slot to form a detent when cooperates with the locking-member handle to hold the handle against the ledge, and to hold the locking member in the closed position.

* * * * *

UNITED STATES PATENT AND TRADEMARK OFFICE
CERTIFICATE OF CORRECTION

PATENT NO. : 4,559,012
DATED : December 17, 1985
INVENTOR(S) : Erwin C. Pletcher It is certified that error appears in the above-identified patent and that said Letters Patent is hereby corrected as shown below:

IN THE SPECIFICATION:

Column 4, line 54, change "when" to -- which --.

Column 6, line 12, change "spacedapart" to -- spaced-apart --.

IN THE CLAIMS:

Column 6, line 35, change "the" (second occurrence) to -- then --.

Signed and Sealed this

Twenty-fourth Day of June 1986

[SEAL]

Attest:

DONALD J. QUIGG

*Attesting Officer*  *Commissioner of Patents and Trademarks*